United States Patent [19]

Urbach et al.

[11] Patent Number: 4,714,708

[45] Date of Patent: Dec. 22, 1987

[54] DERIVATIVES OF CIS, ENDO-2-AZABICYCLO[5.3.0]DECANE-3-CARBOXYLIC ACID, AND THEIR USE FOR TREATING HYPERTENSION

[75] Inventors: Hansjörg Urbach, Kronberg; Rainer Henning, Frankfurt am Main; Volker Teetz, Hofheim am Taunus; Reinhard Becker, Wiesbaden, all of Fed. Rep. of Germany

[73] Assignee: Hoechst Aktiengesellschaft, Fed. Rep. of Germany

[21] Appl. No.: 561,230

[22] Filed: Dec. 14, 1983

[30] Foreign Application Priority Data

Dec. 16, 1982 [DE] Fed. Rep. of Germany ....... 3246503

[51] Int. Cl.$^4$ .................. C07D 209/02; A61K 31/40
[52] U.S. Cl. ..................................... 514/412; 548/452
[58] Field of Search ..................... 548/452; 514/412

[56] References Cited

U.S. PATENT DOCUMENTS 3,113,950  12/1963  Sunagawa et al. .................. 548/576

FOREIGN PATENT DOCUMENTS

| 37231 | 10/1981 | European Pat. Off. |
| 050800 | 5/1982 | European Pat. Off. |
| 79522 | 5/1983 | European Pat. Off. |
| 79022 | 5/1983 | European Pat. Off. |
| 81094 | 6/1983 | European Pat. Off. |
| 90362 | 10/1983 | European Pat. Off. |

Primary Examiner—Robert T. Bond
Assistant Examiner—D. B. Springer
Attorney, Agent, or Firm—Finnegan, Henderson, Farabow, Garrett & Dunner

[57] ABSTRACT

The invention relates to derivatives of cis,endo-2-azabicyclo[5.3.0]decane-3-carboxylic acid of the formula I

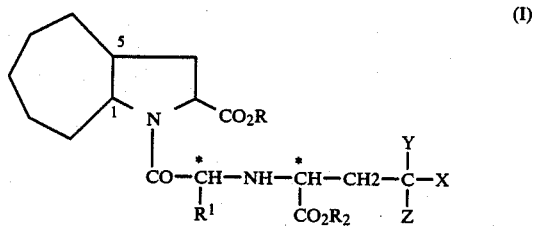

in which R denotes hydrogen, alkyl, alkenyl or aralkyl, $R^1$ denotes hydrogen, allyl, vinyl or a side chain of an optionally protected naturally occurring α-aminoacid, $R^2$ denotes hydrogen, alkyl, alkenyl or aralkyl, Y denotes hydrogen or hydroxyl, Z denotes hydrogen, or Y and Z together denote oxygen, X denotes alkyl, alkenyl, cycloalkyl, aryl which can be substituted once, twice or three times by alkyl, alkoxy, hydroxyl, halogen, nitro, amino, alkylamino, dialkylamino or methylenedioxy, or denotes indol-3-yl, and their physiologically acceptable salts, a process for their preparation, agents containing them and their use.

13 Claims, No Drawings

DERIVATIVES OF CIS, ENDO-2-AZABICYCLO[5.3.0]DECANE-3-CARBOXYLIC ACID, AND THEIR USE FOR TREATING HYPERTENSION

The invention relates to derivatives of cis,endo-2-azabicyclo[5.3.0]decane-3-carboxylic acid of the formula I

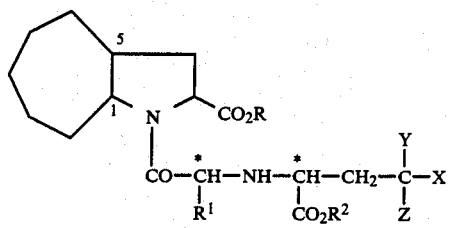

in which the hydrogen atoms on the bridgehead carbon atoms 1 and 5 have the cis-configuration relative to one another and the carboxyl group on C atom 3 is oriented endo to the bicyclic ring system and in which R denotes hydrogen, $(C_1-C_6)$-alkyl, $(C_2-C_6)$-alkenyl or $(C_6-C_{12})$-aryl-$(C_1-C_4)$-alkyl, $R^1$ denotes hydrogen, allyl, vinyl or a side chain of an optionally protected, naturally occurring α-aminoacid $R^1$—CH(NH$_2$)—COOH, $R^2$ denotes hydrogen, $(C_1-C_6)$-alkyl, $(C_2-C_6)$-alkenyl or $(C_6-C_{12})$-aryl-$(C_1-C_4)$-alkyl, Y denotes hydrogen or hydroxyl, Z denotes hydrogen or Y and Z together denote oxygen, X denotes $(C_1-C_6)$-alkyl, $(C_2-C_6)$-alkenyl, $(C_5-C_9)$-cycloalkyl, $(C_6-C_{12})$-aryl, preferably phenyl, which can be substituted once, twice or three times by $(C_1-C_4)$-alkyl, $(C_1-C_4)$-alkoxy, hydroxyl, halogen, nitro, amino, $(C_1-C_4)$-alkylamino, di-$(C_1-C_4)$-alkylamino and/or methylenedioxy, or denotes indol-3-yl, and their physiologically acceptable salts.

Those compounds of the formula I in which

R denotes hydrogen, $R^1$ denotes methyl, the optionally acylated side chain of lysine or the O-alkylated side chain of tyrosine, $R^2$ denotes hydrogen, methyl, ethyl, benzyl or tert.-butyl, X denotes phenyl or phenyl substituted once or twice with fluorine and/or chlorine, Y denotes hydrogen or hydroxyl and Z denotes hydrogen or Y and Z together denote oxygen are preferred. In this context and in the following text, aryl is understood to be preferably phenyl.

Particularly preferred compounds which may be mentioned are:

N-(1-S-carboethoxy-3-phenylpropyl)-S-alanyl-cis,endo-2-azabicyclo[5.3.0]decane-3-S-carboxylic acid, N-(1-S-carboxy-3-phenylpropyl)-S-alanyl-cis,endo-2-azabicyclo[5.3.0]decane-3-S-carboxylic acid, N-(1-S-carboethoxy-3-phenylpropyl)-S-lysyl-cis,endo-2-azabicyclo[5.3.0]decane-3-S-carboxylic acid, N-(1-S-carboxy-3-phenylpropyl)-S-lysyl-cis,endo-2-azabicyclo[5.3.0]decane-3-S-carboxylic acid, N-(1-S-carboethoxy-3-phenylpropyl)-O-ethyl-S-tyrosyl-cis,endo-2-azabicyclo[5.3.0]decane-3-S-carboxylic acid and N-(1-S-carboethoxy-3-phenylpropyl)-O-methyl-S-tyrosyl-cis,endo-2-azabicyclo[5.3.0]decane-3-S-carboxylic acid.

In the case where $R^1$ represents a side chain of a protected naturally occurring α-aminoacid, such as, for example, protected Ser, Thr, Asp, Asn, Glu, Gln, Arg, Lys, Hyl, Cys, Orn, Cit, Tyr, Trp, His or Hyp, then the preferred protective groups are the groups customary in peptide chemistry (cf. Houben-Weyl, Vol. XV/1 and XV (2)). In the case where $R^1$ denotes the protected lysine side chain, the known amino protective groups, but in particular $(C_1-C_6)$-alkanoyl, are preferred. In the case where $R^1$ denotes the protected tyrosine side chain, the protective group on oxygen is an ether protective group, in particular $(C_1-C_6)$-alkyl; methyl and ethyl are particularly preferred protective groups.

Particularly suitable salts are the hydrochlorides, maleates, tartrates and the alkali metal, Ca, Mg and Zn salts.

The centers of chirality at the carbon atoms in the chain and at C atom 3 of the bicyclic system, which are labeled with an asterisk (*), can have either the R or the S configuration. However, those compounds in which these centers have the S configuration are preferred, with the exception that when NH—CHR$^1$—CO=Cys, the R configuration of this center is preferred.

The invention also relates to a process for the preparation of the compounds of the formula I, which comprises reacting a compound of the formula II in which $R^2$ has the meanings mentioned above with the exception of hydrogen with a compound of the formulae IIIa or IIIb or the racemate in which W denotes a group esterifying carboxyl, such as $(C_1-C_6)$-alkyl or $(C_7-C_8)$-aralkyl, preferably tert.-butyl or benzyl, by methods of amide formation known in peptide chemistry optionally converting the compounds of the formula I thus obtained by hydrogen-atom, treatment with acid and/or base into compounds of the formula I (R and/or $R^2$=H), optionally esterifying the compounds thus obtained in a manner known per se and/or optionally converting them into their physiologically acceptable salts.

Diastereomers of the formula I can be separated from one another, for example, by crystallization or chromatography.

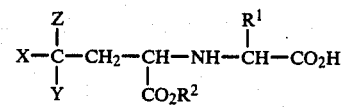

(II)

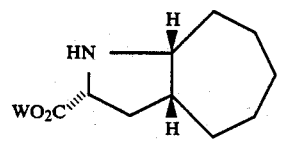

(IIIa)

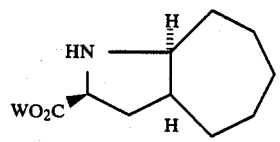

(IIIb)

Compounds of the formula II have already been proposed. Those having X=phenyl, Y=H, Z=H, $R^1$=CH$_3$ and $R^2$=CH$_3$ or C$_2$H$_5$ are known (for example from European Pat. No. 0,037,231) and are accessible by various routes. The benzyl esters ($R^2$=benzyl) can be prepared analogously.

The Mannich reaction of acetophenones of the formulae Iva, in which X represents aryl optionally substituted as above, with glyoxylic esters and α-aminoacid esters leads to compounds of the formula II in which Y and Z together denote oxygen (formula IV). In the formula lv, W' denotes a radical which can be split off by hydrogenolysis, base or acid, preferably benzyl or tert.-butyl and X represents optional meanings as defined above. However, in the case of the benzyl ester (W'=benzyl), $R^2$ must not be benzyl. On hydrogenolysis of these compounds with Pd, compounds of the formula II in which Y and Z are hydrogen are produced.

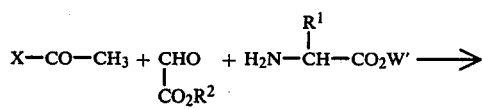

(IVa)

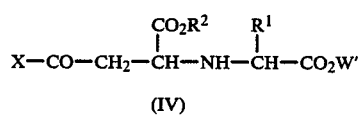

(IV)

Compounds of the formula II. in which Y and Z together denote oxygen can likewise be obtained in high yields by Michael addition of appropriate ketoacrylic esters with α-aminoacid esters. Ester cleavage leads to the same products as the Mannich reaction.

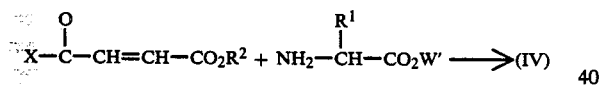

The diastereomers with the preferred S,S-configuration are produced by employing L-alanine esters in excess and can be obtained by crystallization or chromatographic separation of the esters on silica gel.

Cis,endo-2-azabicyclo[5.3.0]decane-3-carboxylic esters of the formula III a and b are accessible from enamines of cycloheptanone having the formula VI in which $X^1$ represents dialkylamino having 2 to 10 carbon atoms or represents a radical of the formula VII in which m and o denote a whole number from 1 to 3, (m+o)≦3 and A denotes CH$_2$, NH, O or S,

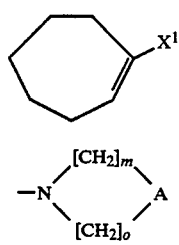

(VI)

(VII)

and N-acylated β-halogeno-α-aminocarboxylic esters of the formula VIII in which $X^2$ represents a nucleofugic group, preferably chlorine or bromine, $Y^1$ represents alkanoyl having 1 to 5 carbon atoms, aroyl having 7 to 9 carbon atoms or other protective groups which can be split off with acid and are customary in peptide chemistry, and $R^2$ represents alkyl having 1 to 5 carbon atoms or aralkyl having 7 to 9 carbon atoms

(VIII)

or with acrylic esters of the formula IX in which $Y^1$ and $R^2$ have the above meaning,

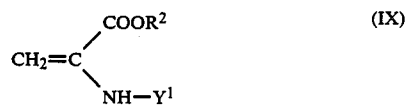

(IX)

by reacting these compounds to give compounds of the formula X in which $R^2$ and $Y^1$ have the above meaning,

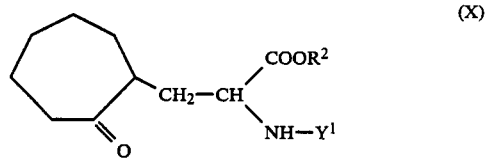

(X)

cyclizing the latter using strong acids, with cleavage of the acylamide and ester, to give compounds of the formula XI a or b,

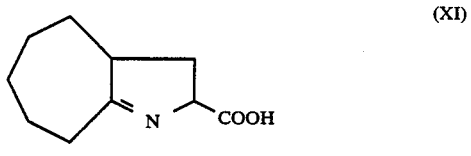

(XI)

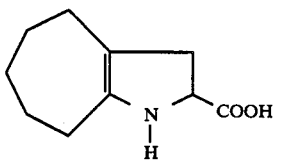

converting the latter by catalytic hydrogenation in the presence of transition metal catalysts or by reduction with bromine-amine complexes or complex borohydrides in lower alcohols into compounds of the formulae IIIa and/or b in which W represents hydrogen, and optionally esterifying to give compounds of the formula III a and/or b in which W represents alkyl having 1 to 6 C atoms or aralkyl leaving 7 to 8 C atoms.

Racemic mixtures comprising compounds of the formulae IIIa and IIIb can, when desired, be separated from one another by the known methods of racemate resolution (cf. for example Quart. Rev. 25 (1971) 323 et seq.).

The bicyclic aminoacids of the formulae IIIa and b have the cis,endo configuration, i.e. the —CO$_2$W group faces towards the cycloheptane ring. All the other 2-azabicyclo[5.3.0]decane-3-carboxylic acid derivatives detailed in the present invention are also in the cis,endo configuration.

Examples of preferred enamines are pyrrolidinocycloheptene and morpholinocycloheptene. The alkylation products of the formula X are preferably cyclized using aqueous hydrochloric acid. The compounds of the formula III a and b (having W=H) or the racemic mixture thereof can be esterified using the methods customary for aminoacids (see, for example, Houben-Weyl, Methoden der organischen Chemie (Methods in Organic Chemistry), Vol. VIII (1952)), for example using thionyl chloride/benzyl alcohol or isobutylene/sulfuric acid. After appropriate working up, compounds of the formula III a and/or b are obtained in the form of the free base or of a salt.

The new compounds of the formula I have a long-lasting and intense hypotensive effect. They are strong inhibitors of angiotensin converting enzyme (ACE inhibitors) and can be employed to control high blood pressure of various etiologies. It is also possible to combine them with other compounds having hypotensive, vasodilator or diuretic activity. Typical representatives of these classes of active compounds are described, for example, in Erhardt-Ruschig, Arzneimittel (Drugs), 2nd edition, Weinheim, FRG, 1972. They can be used intravenously, subcutaneously or orally.

On oral administration, the dose is 1–100 mg, preferably 1–50, in particular 1–30 mg, per single dose for an adult of normal weight, which corresponds to 0.013 to 1.3 mg/kg/day, preferably 0.013 to 0.7 mg/kg/day, in particular 0.013 to 0.4 mg/kg/day. It can also be raised in severe cases, since toxic properties have not hitherto been observed. It is also possible to decrease the dose and this is particularly appropriate when diuretics are administered at the same time.

The compounds according to the invention can be administered orally or parenterally in an appropriate pharmaceutical formulation. For a form for oral use, the active compounds are mixed with the additives customary for this purpose, such as vehicles, stabilizers or inert diluents and converted by customary methods into suitable forms for administration, such as tablets, coated tablets, hard capsules, aqueous alcoholic or oily suspensions or aqueous alcoholic or oily solutions. Examples of inert vehicles which can be used are gum arabic, magnesium carbonate, potassium phosphate, lactose, glucose or starch, especially corn starch. In this context, the formulation can be either as dry or moist granules. Examples of suitable oily vehicles or solvents are vegetable and animal oils, such as sunflower oil or cod-liver oil.

For subcutaneous or intravenous administration, the active compounds or their physiologically tolerated salts are converted into a solution, suspension or emulsion, if desired with the substances customary for this purpose, such as solubilizers, emulsifiers or other auxiliaries. Examples of suitable solvents for the new active compounds and the corresponding physiologically tolerated salts are: water, physiological saline solutions or alcohols, such as ethanol, propanediol or glycerol, in addition sugar solutions, such as solutions of glucose or mannitol, or a mixture of the various solvents mentioned.

The examples below are intended to explain the procedures according to the invention without restricting the invention to the substances mentioned here as representatives.

Unless otherwise indicated, the $^1$H-NMR data relate to CDCl$_3$ solutions and are $\delta$ values.

EXAMPLE I

N-(1-S-Carboethoxy-3-phenylpropyl)-S-alanyl-cis,endo-2-azabicyclo[5.3.0]decane-3-S-carboxylic acid (1) Methyl 2-acetylamino-3-(2-oxocycloheptyl)propionate 25.7 g of methyl 3-chloro-2-acetylaminopropionate and 30 g of cycloheptenopyrrolidine in 170 ml of DMF are maintained at room temperature for 36 hours. The mixture is evaporated in vacuo, the residue is taken up in a little water, the pH is adjusted to 2 with concentrated hydrochloric acid and the mixture is extracted twice with 200 ml of ethyl acetate each time. A pale yellow oil remains after evaporation of the organic phase.

Yield: 44 g $^1$H NMR: 2.1 (s, 3H); 3.7 (s, 3H); 4.4–4.8 (m, 1H)

(2) cis,endo-2-Azabicyclo[5.3.0]decane-3-carboxylic acid hydrochloride 44 g of the acetylamino derivative prepared under (1) in 250 ml of 2N hydrochloric acid are boiled under reflux for 90 minutes. The mixture is evaporated in vacuo, the residue is taken up in glacial acetic acid, 2 g of Pt/C (10% Pt) are added and the mixture is hydrogenated. After filtration, the filtrate is evaporated and the residue is crystallized from ethyl acetate/diisopropyl ether.

Melting point: 252°–256° C. (still contains acetic acid from the NMR)

Yield: 20 g (3) Benzyl cis,endo-2-azabicyclo[5.3.0]decane-3-carboxylate hydrochloride 7.7 g of the carboxylic acid prepared under (2) are added to an ice-cold mixture of 70 ml of benzyl alcohol and 7.1 ml of thionyl chloride and the mixture is left at 5° C. for 48 hours. After evaporation in vacuo, 7.3 g of the benzyl ester crystallizes from diisopropyl ether. $^1$H NMR (of the base in CDCl$_3$, 400 MHz) 1.1–2.0 (m, 11H); 2.1 (s, 1H); 2.2–2.4 (m, 2H); 3.3 (m, 1H); 3.3 (m, 1H); 3.7 (m, 1H); 5.2 (dd, 2H); 7.3 (s, 5H).

(4) Benzyl N-(1-S-carboethoxy-3-phenylpropyl)-S-alanyl-cis,endo-2-azabicyclo[5.3.0]decane-3-S-carboxylate 3.5 g of the benzyl ester prepared according to (3) are brought to reaction with 1.7 g of HOBt, 3.6 g of N-(1-S-carboethoxy-3-phenylpropyl)-S-alanine, 2.7 g of dicyclohexylcarbodiimide and 1.6 ml of N-ethylmorpholine in 15 ml of dimethylformamide. After stirring at room temperature for 10 hours, the precipitated dicyclohexylurea is filtered off, the filtrate is evaporated, the residue is taken up in methylene chloride and the solution is extracted with 2× with saturated NaHCO$_3$ solution. After drying the organic phase, it is evaporated and the crude product obtained (6.3 g) is chromatographed over a column of silica gel using cyclohexane/ethyl acetate in the ratio 2:8. The isomer eluted first is the S,S-compound, and a later eluate provides the S,S,R-compound after evaporation.

R$_f$ of the S,S,S-compound: 0.46 (SiO$_2$; cyclohexane/ethyl acetate 1:4)

R$_f$ of the S,S,R-compound: 0.38

(5) N-(1-S-Carboethoxy-3-phenylpropyl)-S-alanyl-cis,endo-2-azabicyclo[5.3.0]decane-3-S-carboxylic acid hydrochloride 0.5 g of the S,S,S-benzyl ester from (4) is dissolved in 15 ml of ethanol and the benzyl group is removed by hydrogenolysis under atmospheric pressure with the addition of 0.1 g of 10% Pd/C. After the calculated amount of hydrogen has been taken up, the catalyst is filtered off and the filtrate is evaporated in vacuo.

Yield: 0.45 g of oil. This is dissolved in ethanol and the pH is adjusted to 4.5 with ethanolic HCl. The solution is evaporated and the residue is triturated with diisopropyl ether. Melting point: decomposition above 124° C. A zinc complex salt which is particularly stable to heat can be obtained by adding aqueous zinc salts to a concentrated methanolic solution of the title compound (zwitterion).

$^1$H NMR: 0.9–3.1 (m, 24H); 3.2–4.9 (m, 5H); 7.2 (s, 5H)

(6) N-(1-S-Carboethoxy-3-phenylpropyl)-S-alanyl-cis-,endo-2-azabicyclo[5.3.0]decane-3R-carboxylic acid hydrochloride The compound is prepared in analogy to the process in Example I (5) from the S,S,R-benzyl ester from Example I (4).

$^1$H NMR: 1.0–3.1 (m, 24H); 3.3–4.9 (m, 5H); 7.2 (s, 5H).

EXAMPLE II (1) tert.-Butyl cis-endo-2-azabicyclo[5.3.0]decane-3-carboxylate 2.5 g of 2-azabicyclo[5.3.0]decane-3-carboxylic acid hydrochloride from Example I (2) in 25 ml of dioxane are brought to reaction with 25 ml of isobutylene and 2.5 ml of concentrated sulfuric acid. After 10 hours at room temperature, the mixture is made alkaline with sodium hydroxide solution, evaporated in vacuo, 100 ml of water is added and the ester is extracted with ether. After evaporating the ether, 2 g of colorless oil are obtained.

$^1$H NMR: 1.1–2.0 (m, 11H); 1.2 (s, 9H); 2.1 (s, NH); 2.2–2.5 (m, 2H); 3.2–3.4 (m, 1H); 3.6–3.8 (m, 1H).

(2) tert.-Butyl ester of N-(1-S-carbobenzyloxy-3-oxo-3-phenylpropyl)-S-alanine 12.0 g of acetophenone, 17 g of benzyl glyoxylate and 31.7 g of the toluenesulfonate of tert.-butyl ester of S-alanine in 200 ml of glacial acetic acid are heated at 45°–50° C. for 24 to 48 hours. The reaction is followed by thin-layer chromatography and discontinued at the point of optimal conversion. The mixture is thoroughly evaporated in vacuo, basified with aqueous bicarbonate solution and extracted with ethyl acetate. The organic phase is evaporated to as small a volume as possible and the S,S-isomer is crystallized from cyclohexane/petroleum ether. The R,S-compound mostly remains in solution. In order to obtain seeding crystals, it is advisable to chromatograph the crude mixture on silica gel in the system cyclohexane/ethyl acetate 2:1 to which 0.1% of triethylamine is added. The S,S-compound is eluted as the second of the two diastereomers.

9 g are obtained.

| Analysis: $C_{24}H_{29}NO_5$: | | | |
|---|---|---|---|
| | C | H | N |
| calculated | 70.1 | 7.1 | 3.4 |
| found | 70.0 | 6.9 | 3.5 |

(3) N-(1-S-Carbobenzyloxy-3-oxo-3-phenylpropyl)-S-alanine trifluoroacetate 8 g of the Mannich condensation product from (2) are dissolved in 25 ml of anhydrous trifluoroacetic acid and left at room temperature for one hour. The solution is evaporated in vacuo, diisopropyl ether is added and the product is precipitated with petroleum ether. 7.2 g of amorphous substance are obtained.

| Analysis: $C_{22}H_{22}NO_7F_3$: | | | |
|---|---|---|---|
| | C | H | N |
| calculated | 56.3 | 4.7 | 3.0 |
| found | 56.0 | 4.8 | 3.1 |

Molecular weight: 469

(4) tert.-Butyl N-(1-S-carbobenzyloxy-3-oxo-3-phenylpropyl)-S-alanyl-cis,endo-2-azabicyclo[5.3.0]decane-3-carboxylate 3.5 g of the N-substituted alanine from (3) reacts with 2.1 g of tert.-butyl cis,endo-2-azabicyclo[5.3.0]decane-3-carboxylate from Example II (1) in analogy to Example I (4). After chromatography over silica gel, 2 g of the title compound are obtained.

(5) N-(1-S-Carbobenzyloxy-3-oxo-3-phenylpropyl)-S-alanyl-cis,endo-2-azabicyclo[5.3.0]decane-3-carboxylic acid 2 g of the tert.-butyl ester from (4) are dissolved in 50 ml of trifluoroacetic acid and left at room temperature for one hour.

The solution is evaporated in vacuo, the remaining resin is taken up in ethyl acetate and neutralized with aqueous bicarbonate. 1.4 g of the title compound are obtained from the ethyl acetate phase.

| Analysis: $C_{30}H_{36}N_2O_6$ | | | |
|---|---|---|---|
| | C | H | N |
| calculated | 69.2 | 7.0 | 5.4 |
| found | 68.9 | 7.1 | 5.2 |

(6) N-(1-S-Carboxy-3-R,S-hydroxy-3-phenylpropyl)-S-alanyl-cis,endo-2-azabicyclo[5.3.0]decane-3-carboxylic acid 1 g of N-(1-S-carbobenzyloxy-3-oxo-3-phenylpropyl)-S-alanyl-cis,endo-2-azabicyclo[5.3.0]decane-3-carboxylic acid are dissolved in 50 ml of ethanol, 150 mg of Pd/BaSO$_4$ are added and the mixture is hydrogenated under atmospheric pressure. After the calculated amount of hydrogen has been taken up, the mixture is filtered, the filtrate is evaporated and the residue is chromatographed over silica gel using the solvent CHCl$_3$/CH$_3$OH/CH$_3$CO$_2$H 50:20:5.

Yield: 0.6 g (7) N-(1-S-Carbobenzyloxy-3-R,S-hydroxy-3-phenylpropyl)-S-alanyl-cis,endo-2-azabicyclo[5.3.0]decane-3-carboxylic acid 1 g of N-(1-S-carbobenzyloxy-3-oxo-3-phenylpropyl)-S-alanyl-cis,endo-2-azabicyclo[5.3.0]decane-3-carboxylic acid are dissolved in 50 ml of a mixture of acetonitrile and water and reduced with 150 mg of NaBH$_4$. After 12 hours the mixture is evaporated to dryness, neutralized with dilute hydrochloric acid and the title compound is extracted with ethyl acetate. In order to remove boric acid and other impurities, the product is chromatographed over silica gel using the solvent CHCl$_3$/CH$_3$OH/CH$_3$COOH 50:10:5.

EXAMPLE III

General method: Ester hydrolysis to prepare compounds of the formula I with $R^2=H$ 1 g of the appropriate ethyl or benzyl ester of the formula I (R=H) is dissolved in 200 ml of dimethoxyethane. One drop of a dilute indicator solution, for example bromothymol blue, is added and an equivalent amount of 4N KOH (aqueous) is added, with vigorous stirring, over the course of 5 minutes so that the indicator shows a pH of 9–10 at the end of the reaction. The pH is immediately adjusted to 4 with hydrochloric acid, the mixture is evaporated to dryness in vacuo and the residue is taken up in 25 ml of ethyl acetate and filtered. On evaporating the ethyl acetate, the dicarboxylic acids are produced as solid, crystalline or amorphous, compounds.

The yields are between 60 and 95%.

EXAMPLE IIIa

N-(1-S-Carboxy-3-phenylpropyl)-S-alanyl-cis,endo-2-azabicyclo[5.3.0]decane-3-S-carboxylic acid 1 g of N-(1-S-carboethoxy-3-phenylpropyl)-S-alanyl-cis,endo-2-azabicyclo[5.3.0]decane-3-S-carboxylic acid from Example I (5) is hydrolyzed as described under Example III (for 1 hour) and worked up.

Yield: 0.85 g
m/e: 416

EXAMPLE IV

Benzyl ester of N-(1-S-carboethoxy-3-oxo-3-phenylpropyl)-S-alanine 65.7 g of ethyl 4-phenyl-4-oxobutene-2-carboxylate (ethyl benzoylacrylate) are dissolved in 225 ml of ethanol and 1 ml of triethylamine is added. A solution of 70 g of benzyl ester of S-alanine in 90 ml of ethanol is rapidly added dropwise to this solution at room temperature. The solution is stirred at room temperature for 2 hours and then cooled down.

The S,S-isomer crystallizes out.
Yield: 94.3 g
Melting point: 73°–74° C.

EXAMPLE V

N-(1-S-Carboethoxy-3-oxo-3-phenylpropyl)-S-alanine 0.5 g of the compound from Example IV is dissolved in 40 ml of ethanol, 0.1 g of 10% Pd/C is added and the mixture is hydrogenated under atmospheric pressure at room temperature.

Yield: 300 mg
Melting point: 210°–220° C.

$^1$H NMR (DMSO-d$_6$): 1.0–1.4 (t, 6H); 3.2–5.0 (m, 8H); 7.2–8.2 (m, 5H).

EXAMPLE VI

Benzyl N-(1-S-carboethoxy-3-oxo-3-phenylpropyl)-s-alanyl-cis,endo-2-azabicyclo[5.3.0]decane-3-S-carboxylate The compound is prepared from benzyl cis,endo-2-azabicyclo[5.3.0]decane-3-S-carboxylate hydrochloride and N-(1-S-carboethoxy-3-oxo-3-phenylpropyl)-S-alanine from Example V in analogy to the process described in Example I (4).

EXAMPLE VII

N-(1-S-Carboethoxy-3-oxo-3-phenylpropyl)-S-alanyl-cis,endo-2-azabicyclo[5.3.0]decane-3-S-carboxylic acid 1 g of the benzyl ester from Example VI is dissolved in 30 ml of ethanol and hydrogenated with 100 mg of Pd/C (10%) under atmospheric pressure at room temperature. The hydrogenation is discontinued after one mole-equivalent of hydrogen has been taken up. The catalyst is filtered off with suction and the solution is evaporated.

Yield: 600 mg of oil.

$^1$H NMR (DMSO-d$_6$): 1.0–3.0 (m, 19H); 3.2–4.9 (m, 10H); 7.2–8.1 (m, 5H).

EXAMPLE VIII $N_\alpha$-(1-S-Carboethoxy-3-phenylpropyl)-S-lysyl-cis,endo-2-azabicyclo[5.3.0]decane-3-S-carboxylic acid dihydrochloride (1) Benzyl ester of $N_\alpha$-(1-S-Carboethoxy-3-phenylpropyl)-$N_\epsilon$-benzyloxycarbonyl-S-lysine 10 g of ethyl 4-phenyl-4-oxobutene-2-carboxylate are dissolved in 100 ml of ethanol. 19.1 g of the benzyl ester of N-benzyloxycarbonyl-S-lysine and 0.2 g of triethylamine are added to this solution. The solution is stirred at room temperature for 3 hours and then evaporated in vacuo. The oily residue (31 g) is dissolved in isopropanol/diisopropyl ether and cooled down. 13 g of the benzyl ester of $N_\alpha$-(1-S-carboethoxy-3-oxo-3-phenylpropyl)-$N_\epsilon$-benzyloxycarbonyl-S-lysine crystallize.

$\alpha_D^{20} = 3.5°$ (c=1, CH$_3$OH)

$^1$N NMR (CDCl$_3$): 1.0–1.4 (tr, 3H); 1.0–2.0 (m, 9H); 2.0–2.6 (broad s, 1H); 2.9–3.9 (m, 6H); 3.9–4.4 (q, 2H); 4.6–4.9 (broad s, 1H); 5.0–5.2 (doubled s, 4HO 7.1–8.1 (m, 15H).

(2) N-(1-S-Carboethoxy-3-phenylpropyl)-N-benzyloxycarbonyl-S-lysine 4.0 g of the lysine benzyl ester derivative prepared in Example VIII (1) are dissolved in 50 ml of glacial acetic acid, and 0.6 g of Pd/C (10%) and 0.6 g of concentrated sulfuric acid are added to this solution. The mixture is hydrogenated under atmospheric pressure at room temperature for 6 hours. The catalyst is then filtered off with suction and the ethanolic solution is stirred with 1.4 g of solid sodium bicarbonate. The solution is evaporated in a rotary evaporator and the residue is dissolved in water. The aqueous phase is extracted with ethyl acetate and methylene chloride. The organic phases are discarded and the aqueous phase is evaporated to dryness in vacuo. The residue is extracted by stirring with methanol. After evaporating the methanol, there remains an oily residue which solidifies on treatment with diisopropyl ether. Yield of $N_\alpha$-(1-S-carboethoxy-3-phenylpropyl)-S-lysine: 2.0 g $^1$H NMR (D$_2$O): 1.0–1.4 (tr, 3H); 1.0–2.5 (m, 9HO, 2.5–4.4 (m, 9H); 3.9–4.4 (q, 2H); 4.5–5.0 (m, 1H); 7.1–7.6 (m, 5H).

m/e: 336

3.4 g of $N_\alpha$-(1-S-Carboethoxy-3-phenylpropyl)-S-lysine are dissolved in 30 ml of methylene chloride and cooled down to 0° C. 2.1 g of triethylamine are added to this solution while cooling in ice and then 1.9 g of benzyl chloroformate are added dropwise. The mixture is stirred at 0° C. for 1 hour and then warmed to room temperature. The methylene chloride solution is then extracted by shaking with water, sodium carbonate solution and water. After drying, the solution is evaporated and the oily residue is chromatographed over silica gel using methylene chloride/methanol.

2.0 g of $N_\alpha$-(1-S-carboethoxy-3-phenylpropyl)-$N_\epsilon$-benzyloxycarbonyl-S-lysine are obtained.

$^1$H NMR (CDCl$_3$/D$_2$O): 1.0–1.4 (tr, 3H); 1.0–2.5 (m, 9H); 2.5–4.4 (m, 9H); 3.9–4.4 (q, 2H); 4.4–5.0 (m, 1H); 5.1 (s, 2H); 7.1–7.5 (m, 10H).

(3) Benzyl $N_\alpha$-(1-S-Carboethoxy-3-phenylpropyl)-$N_\epsilon$-benzyloxycarbonyl-S-lysyl-cis,endo-2-azabicyclo[5.3.0]decane-3-S-carboxylate (a) 560 mg of benzyl 2-azabicyclo[5.3.0]decane-3-carboxylate hydrochloride, prepared in accordance with Example I (3), are reacted in analogy to Example I (4) with 940 mg of $N_\alpha$-(1-S-Carboethoxy-3-phenylpropyl)-$N_\epsilon$-benzyloxycarbonyl-S-lysine, prepared in accordance with Example VIII (2). After working up, 1.5 g of oil which is a mixture of two diastereomeric compounds are obtained.

The mixture of diastereomers is separated into the individual components by column chromatography with silica gel and cyclohexane/ethyl acetate 2:1 as the eluting agent. The isomer which is eluted first is the above compound. 0.6 g of oil is obtained.

$^1$H NMR (CDCl$_3$) after H/D exchange with D$_2$O: 1.0–2.6 (m, 24H); 2.6–4.5 (m, 8H); 4.6–5.0 (m, 2H); 5.1–5.3 (doubled s, 4H); 7.1–7.6 (m, 15H).

(b) The later eluate provides 0.4 g of benzyl $N_\alpha$-(1-S-carboethoxy-3-phenylpropyl)-$N_\epsilon$-benzyloxycarbonyl-S-lysyl-cis,endo-2-azabicyclo[5.3.0]decane-3-R-carboxylate.

$^1$H NMR (CDCl$_3$) (after H/D exchange with D$_2$O): 1.0–2.6 (m, 24H); 2.6–4.4 (m, 8H); 4.5–5.0 (m, 2H); 5.1–5.3 (doubled s, 4H); 7.1–7.5 (m, 15H).

(4) $N_\alpha$-(1-S-Carboethoxy-3-phenylpropyl)-S-lysyl-cis,endo-2-azabicyclo[5.3.0]decane-3-S-carboxylic acid dihydrochloride 500 mg of benzyl $N_\alpha$-(1-S-carboethoxy-3-phenylpropyl)-$N_\epsilon$-benzyloxycarbonyl-S-lysyl-cis,endo-2-azabicyclo[5.3.0]decane-3-S-carboxylate from Example VIII (3a) are dissolved in 20 ml of ethanol and the benzyl group is removed by hydrogenolysis under atmospheric pressure with the addition of 0.1 g of 10% Pd/C. After completion of hydrogen uptake, the catalyst is filtered off, ethanolic hydrogen chloride solution is added to the ethanolic solution to pH 1 and the ethanol is evaporated in vacuo. Diisopropyl ether is added to the residue whereupon the product solidifies. 200 mg are obtained.

$^1$H NMR of the betain (CDCl$_3$, after H/D exchange with D$_2$O): 1.0–2.5 (m, 24H); 2.6–4.4 (m, 8H); 4.4–4.9 (m, 2H); 7.2 (s, 5H).

EXAMPLE IX $N_\alpha$-(1-S-Carboethoxy-3-phenylpropyl)-S-lysyl-cis,endo-2-azabicyclo[5.3.0]decane-3-R-carboxylic acid dihydrochloride 0.3 mg of the appropriate benzyl ester from Example VIII (3b) are reacted in analogy to Example VIII (4) and worked up. 130 mg of the carboxylic acid are obtained as the dihydrochloride.

$^1$H NMR of the betaine (CDCl$_3$, after H/D exchange with D$_2$O): 1.0–2.6 (m, 24H); 2.6–4.4 (m, 8H); 4.4–4.8 (m, 2H); 7.2 (s, 5H).

EXAMPLE X $N_\alpha$-(1-S-Carboxy-3-phenylpropyl)-S-lysyl-cis,endo-2-azabicyclo[5.3.0]decane-3-S-carboxylic acid hydrochloride 0.5 g of $N_\alpha$-(1-S-Carboethoxy-3-phenylpropyl)-S-lysyl-cis,endo-2-azabicyclo[5.3.0]decane-3-S-carboxylic acid dihydrochloride from Example VIII (4) are suspended in 20 ml of dimethoxyethane. The suspension is stirred for half an hour. The pH is then adjusted to 4 with hydrochloric acid, the mixture is evaporated to dryness in vacuo and the residue is taken up in ethyl acetate and the mixture is filtered. The ethyl acetate solution is evaporated and the residue is triturated with diisopropyl ether whereupon it solidifies.

Yield: 0.30 g $^1$H NMR (D$_2$O): 1.2–2.5 (m, 21H); 2.5–4.5 (m, 6H); 4.5–4.9 (m, 2H); 7.2 (s, 5H).

EXAMPLE XI $N_\alpha$-(1-S-Carboxy-3-phenylpropyl)-s-lysyl-cis,endo-2-azabicyclo[5.3.0]decane-3-R-carboxylic acid hydrochloride 500 mg of $N_\alpha$-(1-S-Carboethoxy-3-phenylpropyl)-S-lysyl-cis,endo-2-azabicyclo[5.3.0]decane-3-R-carboxylic acid dihydrochloride from Example IX are hydrolyzed and worked up in analogy to Example X.

Yield: 0.30 g $^1$H NMR (D$_2$O): 1.2–2.5 (m, 21H); 2.5–4.5 (m, 6H); 4.5–4.9 (m, 2H); 7.2 (s, 5H).

EXAMPLE XII

N-(1-S-Carboethoxy-3-phenylpropyl)-O-ethyl-S-tyrosyl-cis,endo-2-azabicyclo[5.3.0]decane-3-S-carboxylic acid (1) Benzyl ester of N-(1-R,S-carboethoxy-3-phenylpropyl)-O-ethyl-S-tyrosine In analogy to Example IV, 24 g of ethyl benzoylacrylate in 100 ml of ethanol are reacted with 30 g of the benzyl ester of O-ethyl-S-tyrosine in the presence of 0.5 ml of triethylamine and, after evaporation of the solution and digestion of the residue with diethyl ether/petroleum ether (1:1) and drying in vacuo, 42 g of the RS,S-compound are obtained.

(2) N-(1-R,S-Carboethoxy-3-phenylpropyl)-O-ethyl-S-tyrosine 40 g of the compound obtained in accordance with XII (1) are hydrogenated in 800 ml of acetic acid with 4 g of Pd/C (10%) under 100 bar pressure and at room temperature. The yield after chromatography on silica gel using the eluting agent ethyl acetate/cyclohexane (1:3) and drying the residue on evaporation is 25 g of title compound which is almost homogeneous by thin layer chromatography. Melting point 205°–213° C.

C$_{23}$H$_{29}$NO$_5$ (399.5): calculated: C 69.15, H 7.31, N 3.50, found: C 69.5, H 7.4, N 3.3.

(3) N-(1-S-Carboethoxy-3-phenylpropyl)-O-ethyl-S-tyrosyl-cis,endo-2-azabicyclo[5.3.0]decane-3-S-carboxylic acid 1 g of the free benzyl ester obtained in accordance with Example I (3) followed by extraction from alkaline solution with diethyl ether is reacted in analogy to Example I (4) with 1.6 g of the compound obtained in accordance with XII (2) using 0.9 g of dicyclohexylcarbodiimide in the presence of 0.55 g of 1-hydroxybenzotriazole. After the chromatography described under Example I (4), 0.7 g of oily benzyl ester is obtained as an intermediate product.

The $^1$H NMR and mass spectra are consistent with the structure indicated.

The benzyl ester is catalytically hydrogenated on Pd(C) in 15 ml of ethanol under atmospheric pressure. After filtering off the catalyst and distilling out the solvent, there remains a solid residue which is digested with diethyl ether/petroleum ether and dried.

Yield: 0.4 g $^1$H NMR (CDCl$_3$): 1.2–3.0 (m, 19H); 1.27 (t, 3H); 1.4 (t, 3H) 3.0–4.3 (m, 4H); 3.8–4.2 (m, 4H); 6.5–7.1 (2d, 4H); 7.3 (s, 5H).

EXAMPLE XIII

N-(1-S-Carboethoxy-3-phenylpropyl)-O-methyl-S-tyrosyl-cis,endo-2-azabicyclo[5.3.0]decane-3-S-carboxylic acid The procedure is as described in Example XII but, in the step analogous to XII (1), the benzyl ester of O-methyl-S-tyrosine is employed, and the title compound is obtained, the $^1$H NMR spectrum of which is consistent with the structure indicated.

We claim:

1. A compound of the formula I

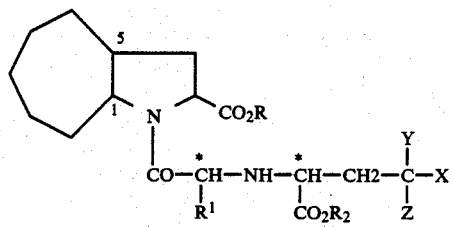

(I)

in which the hydrogen atoms on the bridgehead C atoms 1 and 5 have the cis-configuration relative to one another and the carboxyl group on C atom 3 is oriented endo to the bicyclic ring system and in which R denotes hydrogen, (C$_1$–C$_6$)-alkyl, (C$_2$–C$_6$)-alkenyl or (C$_6$–C$_{12}$)-aryl-(C$_1$–C$_4$)-alkyl, R$^1$ denotes hydrogen, allyl, vinyl or a side chain of an optionally protected, naturally occurring α-amino-acid R$^1$CH(NH$_2$)—COOH, R$^2$ denotes hydrogen, (C$_1$–C$_6$)-alkyl, (C$_2$–C$_6$)-alkenyl or (C$_6$–C$_{12}$)-aryl-(C$_1$–C$_4$)-alkyl, Y denotes hydrogen or hydroxyl, Z denotes hydrogen or Y and Z together denote oxygen, X denotes (C$_1$–C$_6$)-alkyl, (C$_2$–C$_6$)-alkenyl, (C$_5$–C$_9$)-cycloalkyl, (C$_6$–C$_{12}$)-aryl which can be substituted once, twice or three times by at least one member selected from the group consisting of (C$_1$–C$_4$)-alkyl, (C$_1$–C$_4$)-alkoxy, hydroxyl, halogen, nitro, amino, (C$_1$–C$_4$)-alkylamino, di-(C$_1$–C$_4$)-alkylamino and methylenedioxy, or denotes indol-3-yl, and its physiologically acceptable salts.

2. A compound of the formula I as claimed in claim 1 in which

R denotes hydrogen,

R$^1$ denotes methyl, the optionally acylated side chain of lysine or the O-alkylated side chain of tyrosine, R$^2$ denotes hydrogen, methyl, ethyl, benzyl or tert.-butyl, X denotes phenyl or phenyl substituted once or twice with at least one member selected from the group consisting of fluorine and chlorine, Y denotes hydrogen or hydroxyl, Z denotes hydrogen or Y and Z together denote oxygen.

3. The compound according to claim 2 which is N-(1-S-Carboethoxy-3-phenylpropyl)-S-alanyl-cis,endo-2-azabicyclo[5.3.0]decane-3-S-carboxylic acid or its physioyogically acceptable salts.

4. The compound according to claim 2 which is N-(1-S-Carboxy-3-phenylpropyl)-S-alanyl-cis,endo-2-azabicyclo[5.3.0]decane-3-S-carboxylic acid or its physiologically acceptable salts.

5. The compound according to claim 2 which is N-(1-S-Carboethoxy-3-phenylpropyl)-S-lysyl-cis,endo-2-azabicyclo[5.3.0]decane-3-S-carboxylic acid or its physiologically acceptable salts.

6. The compound according to claim 2 which is N-(1-S-Carboxy-3-phenylpropyl)-S-lysyl-cis,endo-2-azabicyclo[5.3.0]decane-3-S-carboxylic acid or its physiologically acceptable salts.

7. The compound according to claim 2 which is N-(1-S-Carboethoxy-3-phenylpropyl)-O-ethyl-S-tyrosyl-cis,endo-2-azabicyclo[5.3.0]decane-3-S-carboxylic acid or its physiologically acceptable salts.

8. The compound according to claim 2 which is N-(1-S-Carboethoxy-3-phenylpropyl)-O-methyl-S-tyrosyl-cis,endo-2-azabicyclo[5.3.0]decane-3-S-carboxylic acid or its physiologically acceptable salts.

9. A compound of the formulae IIIa and/or IIIb

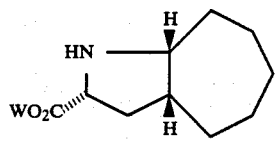

(IIIa)

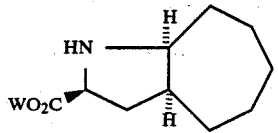

(IIIb)

in which W denotes hydrogen, alkyl having 1–6 carbon atoms or aralkyl having 7 or 8 carbon atoms, and its salts with physiologically acceptable acids and (in the case where W=hydrogen) with physiologically acceptable bases.

10. A compound as claimed in claim 9, wherein, in formulae IIIa and b, W denotes hydrogen, tert.-butyl, benzyl or nitrobenzyl.

11. A pharmaceutical composition comprising an effective amount of a compound or a mixture of compounds according to claim 1 or a physiologically acceptable salt thereof and a physiologically acceptable carrier.

12. A method of treating hypertension by administering an effective amount of a compound according to claim 1 or a physiologically acceptable salt thereof.

13. A compound of the formula I as claimed in claim 1 in which X denotes phenyl.

* * * * *

UNITED STATES PATENT AND TRADEMARK OFFICE
CERTIFICATE OF CORRECTION

PATENT NO. : 4,714,708

DATED : December 22, 1987

INVENTOR(S) : Hansjorg URBACH, et al.

It is certified that error appears in the above-identified patent and that said Letters Patent is hereby corrected as shown below:

In Claim 3, Column 14, Line 12; change

"physioyogically" to --physiologically--.

Signed and Sealed this

Twenty-fifth Day of October, 1988

Attest:

DONALD J. QUIGG

Attesting Officer

Commissioner of Patents and Trademarks